US012778645B2

(12) United States Patent
Verhaegh et al.

(10) Patent No.: US 12,778,645 B2
(45) Date of Patent: Nov. 3, 2026

(54) BONE NAIL DEVICE

(71) Applicant: Osseointegration International B.V., Ruurlo (NL)

(72) Inventors: Franciscus Theodorus Peter Verhaegh, Doesburg (NL); Munjed Al Muderis, Nort Ryde (AU)

(73) Assignee: Osseointegration International B.V., Ruurlo (NL)

( * ) Notice: Subject to any disclaimer, the term of this patent is extended or adjusted under 35 U.S.C. 154(b) by 431 days.

(21) Appl. No.: 18/002,277

(22) PCT Filed: Jul. 1, 2021

(86) PCT No.: PCT/NL2021/050411

§ 371 (c)(1),
(2) Date: Dec. 19, 2022

(87) PCT Pub. No.: WO2022/005282

PCT Pub. Date: Jan. 6, 2022

(65) Prior Publication Data

US 2023/0338065 A1 Oct. 26, 2023

(30) Foreign Application Priority Data

Jul. 3, 2020 (NL) ...................................... 2025981

(51) Int. Cl.
*A61B 17/72* (2006.01)
*A61B 17/00* (2006.01)
(Continued)

(52) U.S. Cl.
CPC .......... *A61B 17/7216* (2013.01); *A61B 34/73* (2016.02); *A61B 2017/00411* (2013.01); *A61B 2017/681* (2013.01)

(58) Field of Classification Search
None
See application file for complete search history.

(56) References Cited

U.S. PATENT DOCUMENTS 5,263,955 A * 11/1993 Baumgart .......... A61B 17/7216 606/62
6,245,075 B1 * 6/2001 Betz .................. A61B 17/7216 606/90

(Continued)

FOREIGN PATENT DOCUMENTS

JP 3338944 B2 * 10/2002 ......... A61B 17/7002
WO 98/30163 A1 7/1998

(Continued)

OTHER PUBLICATIONS

English language translation of JP-3338944-B2 (machine translation) (Year: 2002).*

*Primary Examiner* — Eduardo C Robert
*Assistant Examiner* — Anna V. Little
(74) *Attorney, Agent, or Firm* — Ipsilon USA—NLO

(57) ABSTRACT

Bone nail device (1), with an outer tubing (2) having an inner screw thread (2*a*) extending over at least a part of an inner surface of the outer tubing (2), and a first bone connection member (2*b*), and an inner tubing (3) having a second bone connection member (3*a*). The inner tubing (3) is arranged inside at least a part of the outer tubing (2) to allow a sliding axial relative movement. A drive unit is present, with a drive motor (7) fixedly attached to the inner tubing (3), and a transport screw (4) having an outer screw thread (4*a*) engaging the inner screw thread (2*a*) of the outer tubing (2). A planetary gear (6) is provided in the drive unit having an input end connected to the drive motor (7) and an output end connected to the transport screw (4).

15 Claims, 5 Drawing Sheets

Figure 1:
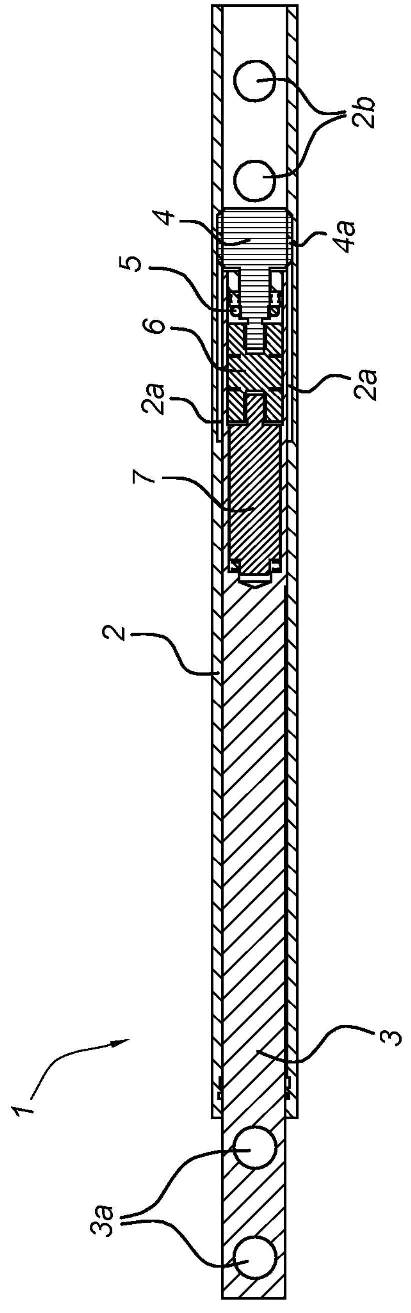

(51) Int. Cl.
*A61B 17/68* (2006.01)
*A61B 34/00* (2016.01)

(56) References Cited

U.S. PATENT DOCUMENTS

| | | | | |
|---|---|---|---|---|
| 7,753,915 | B1 * | 7/2010 | Eksler | A61B 17/7016 606/86 R |
| 8,632,544 | B2 | 1/2014 | Haaja et al. | |
| 2008/0108995 | A1 * | 5/2008 | Conway | A61B 17/7216 606/63 |
| 2011/0196435 | A1 * | 8/2011 | Forsell | A61B 17/7216 606/86 R |
| 2011/0230883 | A1 * | 9/2011 | Zahrly | A61B 17/7225 606/63 |
| 2012/0130428 | A1 * | 5/2012 | Hunziker | A61B 17/7016 606/258 |
| 2012/0179215 | A1 * | 7/2012 | Soubeiran | A61B 17/7216 606/86 R |
| 2012/0209265 | A1 | 8/2012 | Pool | |
| 2012/0209269 | A1 * | 8/2012 | Pool | A61B 17/725 606/63 |
| 2013/0072932 | A1 * | 3/2013 | Stauch | A61B 17/7241 606/63 |
| 2014/0031870 | A1 * | 1/2014 | Chang | A61B 17/705 606/264 |
| 2014/0114311 | A1 * | 4/2014 | Pool | A61B 17/8872 606/62 |
| 2015/0105834 | A1 * | 4/2015 | Bilger | A61B 17/7016 606/86 R |
| 2015/0313745 | A1 * | 11/2015 | Cheng | A61B 17/7216 602/19 |
| 2018/0132900 | A1 * | 5/2018 | Fening | A61B 17/7016 |
| 2019/0328425 | A1 * | 10/2019 | Sharifi-Mehr | A61B 17/8023 |
| 2019/0336183 | A1 * | 11/2019 | Farley | A61B 17/846 |

FOREIGN PATENT DOCUMENTS

| | | | | | |
|---|---|---|---|---|---|
| WO | WO-0143652 | A1 * | 6/2001 | A61B 17/7225 |
| WO | WO-2010134078 | A1 * | 11/2010 | F16H 25/2204 |
| WO | WO-2012003555 | A1 * | 1/2012 | A61B 17/7225 |

* cited by examiner 2
2d
3a
3b
3
7
6
2a
5
4
4a
2b 2b
3a
3b
2
3
7
6
5
4
4a
2a 2c
2d
2
3a
3b
3
7
6
2a
5
4
4a
2b

BONE NAIL DEVICE

FIELD OF THE INVENTION

The present invention relates to a bone nail device, fixable to at least two parts of an elongate bone and having two parts which can move relative to another in an axial direction. The bone nail device can be utilized to move two bone parts relative to each other, e.g. for use during a bone fracture recovery or other treatments for bone extension, bone compression and/or bone transport.

BACKGROUND ART

International patent publication WO98/30163 discloses a distraction device for moving apart two bone sections, in particular for extending bones or bridging a gap in a bone. The distraction device has an intramedullary nail which can be introduced into the medullary space of a bone and comprises two parts which can be moved axially and can each be secured to one of the two bone sections. The distraction device further has a drive unit that drives a drive shaft, and a device for converting the rotational movement of the drive shaft into a relative axial movement of the two parts of the intramedullary nail. The drive shaft drives planetary rollers which are held on orbits on which they engage by means of drive grooves provided on their outer periphery in corresponding drive grooves in a hollow body surrounding the planetary rollers.

SUMMARY OF THE INVENTION

The present invention seeks to provide a bone distraction device for improved bone extension, bone compression and/or bone transport, based on a bone nail device comprising an inner tube being arranged inside an outer tube.

According to the present invention, a bone nail device is provided, comprising an outer tubing having an inner screw thread extending over at least a part of an inner surface of the outer tubing, and a first bone connection member, an inner tubing having a second bone connection member, the inner tubing being arranged inside at least a part of the outer tubing to allow a sliding axial relative movement (e.g. by having an outer diameter of the inner tubing being smaller than an inner diameter of the outer tubing), and a drive unit. The drive unit comprises a drive motor fixedly attached to the inner tubing, a transport screw having an outer screw thread engaging the inner screw thread of the outer tubing, and a planetary gear having an input end connected to the drive motor and an output end connected to the transport screw. The present invention embodiments have the advantage that it is possible to integrate the drive parts (drive motor, transport screw and planetary gear) within the bone nail device and moving along with the inner tubing, allowing to use minimal dimensions, as low as possible complexity and ease of placement in many bone surgery applications. Furthermore, a sufficient high load may be applied, depending on the exact application of the bone nail device. Operation of the bone nail device is possible after placement without obstruction or interfering with tissue surrounding the bone.

SHORT DESCRIPTION OF DRAWINGS

The present invention will be discussed in more detail below, with reference to the attached drawings, in which FIG. 1 shows a cross sectional view of a bone nail device for bone extension, bone compression and/or bone transport, according to an embodiment of the present invention;

FIGS. 2A-2F show a cross sectional view of a bone nail device for bone extension, bone compression and/or bone transport, according to six exemplary embodiments of the present invention; and FIGS. 3A-3F show a cross sectional view of a bone nail device for bone extension, bone compression and/or bone transport, according to six further exemplary embodiments of the present invention.

DESCRIPTION OF EMBODIMENTS

Distraction osteogenesis, also known as bone distraction, is a well-established surgical procedure used for treating the skeletal system, and in particular, treatments relating to bone fractures or bone reconstruction. In bone distraction, two sections of a bone are separated at a specific distraction rate, where the distraction rate varies between 0 mm to a few mm per day. Due to the natural healing process, new bone is formed in the gap between the two sections, and the bone is consolidated.

Bone distraction can be used for the purposes of bone extension. For example, a patient may have an asymmetric pair of limbs, where one limb is longer than the other, originating from a discrepancy in the limb growth during maturity. In this case, extension of the shorter limb to match the longer limb is desirable. The shorter limb would be purposely fractured into two parts, and by using bone distraction, the two parts are separated to extend the limb until the desired length.

Similarly, bone distraction can be used for the purposes of bone transport. For example, a patient may have a bone infection originating from a previous fracture, leading to the infected part of the bone being removed. In this case, a gap in the bone may be present, and forming new bone in the gap is desirable. The bone would be purposely fractured, and by using bone distraction, the bone can be transported to fill the gap with the missing bone.

In further applications, it is necessary to keep two bone parts together under a specific compression force, in order to allow healing of a fracture under the right circumstances.

Given the well-established nature of bone distraction in the surgical field, a variety of devices are known in the art for bone extension, bone compression and/or bone transport purposes. Intramedullary nails are a common example of such devices. Typically, intramedullary nails are cylindrical, and are implanted within the medullary cavity of the bone. These devices can generally be characterised in having two or more parts, arranged coaxially in a telescope arrangement, where at least two parts of the device are connected to a part of a fractured bone. With use of a drive motor, the two or more parts of the intramedullary nail can be moved axially apart relative to one another, thereby performing bone extension, bone compression or bone transport.

Although intramedullary nails have been successfully used to perform bone distraction, these devices still have their drawbacks. For example, the need for adjustment of the length of the intramedullary nail after placement remotely requires the use of complicated drive arrangements. As such, there is a need in the art to overcome these drawbacks and provide a bone nail device having a drive arrangement of simple structure and reliable operation.

For other bone extension applications, all parts of the intramedullary nail may have to move from one another, extending the device and thus increasing the overall length of the device. Given the placement of the bone fracture and/or connection to the bone, this can limit with the desired length of the bone extension. Furthermore, the extension of the intramedullary nail may also not be sufficiently guided, where if a small misalignment is present, this can cause bone extension, bone compression or bone transport of an incorrect trajectory.

The present invention embodiments provide a bone nail device for improved bone distraction, allowing for bone extension, bone compression and/or bone transport. In further embodiments, reducing or at least lessening the requirements to the device dimensions (mainly the desired length) is accomplished, and in even further embodiments, bone extension, bone compression and/or bone transport can be accomplished with a guided trajectory, even with an arched or contoured trajectory.

FIG. 1 shows a cross sectional view of a bone nail device 1 suitable for bone extension, bone compression and/or bone transport, according to an embodiment of the present invention. The bone device 1 comprises an outer tubing 2, and an inner tubing 3 being arranged inside at least a part of the outer tubing 2 to allow a sliding axial relative movement. The inner tubing 3 thereby has an outer diameter that is less than the inner diameter of the outer tubing 2, allowing, for example, the inner tube 3 to smoothly move away from or towards the outer tubing 2. The outer tubing 2 has a first bone connection member 2*b*. and the inner tubing 3 has a second bone connection member 3*a*. The first and second bone connection member 2*b*, 3*a* are arranged to be connected to separate bone parts with a secure attachment (e.g. using screws). In a specific embodiment, the first and/or second bone connection member 2*b*, 3*a*, comprise an aperture for accommodating a transverse bone fixation screw. The aperture may, for example, comprise a screw thread, to easily allow a screw to be screwed through the aperture into at least a part of the bone, allowing secure fixation of the first and/or second connection member 2*b*, 3*a* to respective bone parts. It is noted that the first and second connection members 2*b*, 3*a* comprise two apertures in the embodiment shown in FIG. 1, but in general, FIG. 1 only shows an exemplary embodiment, and the first and/or second connection members 2*b*, 3*a* may comprise more or fewer apertures in further embodiments.

In the bone nail device 1, in general the outer tubing 2 has an inner screw thread 2*a* extending over at least a part of an inner surface of the outer tubing 2, and the bone nail device 1 further comprises a drive unit comprising a drive motor 7 fixedly attached to the inner tubing 3, a transport screw 4 having an outer screw thread 4*a* engaging the inner screw thread 2*a* of the inner tubing 3, and a planetary gear 6 having an input end connected to the drive motor 7 and an output end connected to the transport screw 4. The configuration of the features as described, and their mechanical connections thereof, allows a sliding, axial movement of the inner tubing 3 relative to the outer tubing 2. Furthermore, the use of the transport screw 4 in this configuration obviates the need for an extension rod or spindle axis running along the entire length of the bone extraction nail device 1 when fitted with a spindle drive mechanism for extraction.

In the exemplary embodiment shown in FIG. 1, the combination of the drive motor 7, the transport screw 4 and the planetary gear 6 is positioned between the first bone connection member 2*b* and the second bone connection member 3*a*. This allows this combination to move along with the inner tube 3, providing a very compact and simple construction of the bone nail device 1.

In the embodiment shown in FIG. 1, a bearing 5 is attached to the transport screw 4 for withstanding axial load, and for allowing a rotation of the transport screw 4 with respect to the inner tubing 3. The bearing 5 further reduces the friction between the transport screw 4 and the inner tube 3, allowing for an easier rotation of the transport screw 4. The bearing 5 also allows for proper structural guidance of the axial load forces applied during operation of the bone nail device 1. A torque can be applied on the transport screw 4 to cause a rotation of the transport screw 4 around its axis. The torque is applied by the output end of the planetary gear 6 that is connected to the transport screw 4, via a drive motor 7 that is connected to the input end of the planetary gear 6. A rotation of the transport screw 4 around its axial axis allows the outer screw thread 4*a* to engage with the inner screw thread 2*a* of the outer tubing 2.

As the transport screw 4 is connected via the planetary gear 6 to the drive motor 7, and the drive motor 7 is fixedly attached to the inner tubing 3, this allows a sliding axial movement of the inner tubing 3 relative to the outer tubing 2 as result from a rotation of the transport screw 4.

In this regard, the inner tubing 3 may move either away from the outer tubing 2, i.e. the inner tubing 3 withdraws from the outer tubing 2, thereby extending the overall length of the bone device 1, or the inner tubing 3 may move towards the outer tubing 2, i.e. the inner tubing 3 slides into the outer tubing 2, thereby reducing the overall length of the bone nail device 1. These relative movements allow for bone extension, bone compression and/or bone transport. The movement of the inner tube 3 to extend or reduce the overall length of the bone nail device 1 depends on the handedness of the inner and outer screw threads 2*a*, 4*a*, and the direction of the rotation of the transport screw 4.

For example, the bone nail device 1, as shown in FIG. 1, may be surgically implanted within the medullary cavity of a bone, where the first bone connection member 2*b* is connected to a first part of a two-part fractured bone, and the second bone connection member 3*a* is connected to a second part of the two-part fractured bone. The transport screw 4 can be rotated such that the direction of the rotation allows the inner tubing 3 to move away from the outer tubing 2, thereby allowing the first part of the two-part fractured bone to move away from the second part of the two-part fractured bone, where the second part of the two-part fractured bone remains in the same position. New bone is formed in the gap between the two parts of the fractured bone, thereby performing bone extension.

In the embodiment shown in FIG. 1, the planetary gear 6 controls the transfer of torque that is applied to the transport screw 4 from the drive motor 7. For example, the planetary gear 6 could be a reduction gear, where the rotation speed of the transport screw 4 is reduced (and the torque applied to the transport screw 4 from the drive motor 7 is increased), and as such, the planetary gear 6 may decrease the rate of bone extension, bone compression and/or bone transport.

Furthermore, the drive motor 7 is an electric motor in a further embodiment, which can be supplied with power via, for example, induction transfer such as wireless energy transfer. Other examples where the drive motor 7 can be supplied with power could be via a direct wired connection with an internal power storage component, such as a battery, implanted within the patient's body itself, or via a direct wired connection with an external power source in the external environment outside of the patient's body. Alternatively, the drive motor 7 could a magnetic motor driven by an external magnetic drive actuator. For example, the drive motor 7 may comprise a permanent magnet motor, where an externally applied alternating magnetic field can force the drive motor 7 into rotation.

In more general wording, the present invention embodiments relate to a bone nail device 1 for bone extension, bone compression and/or bone transport, comprising an outer tubing 2 having an inner screw thread 2*a* extending over at least a part of an inner surface of the outer tubing 2, and a first bone connection member 2*b*, an inner tubing 3 having a second bone connection member 3*a*, the inner tubing 3 being arranged inside at least a part of the outer tubing 2 to allow a sliding axial relative movement. The bone nail device 1 further comprises a drive unit, the drive unit comprising a drive motor 7 fixedly attached to the inner tubing 3, a transport screw 4 having an outer screw thread 4*a* engaging the inner screw thread 2*a* of the outer tubing 2, and a planetary gear 6 having an input end connected to the drive motor 7 and an output end connected to the transport screw 4. The first and second bone connection members 2*b*, 3*a* can be connected to at least two parts of a fractured bone, and by rotating the transport screw 4, the inner tubing 3 moves relative to the outer tubing 2, allowing at least one part of the fractured bone to move relative to at least one other part of the fractured bone, thereby performing bone extension, bone compression and/or bone transport. The drive unit can be accommodated entirely within the outer tubing 2, enabling a proper intramedullary positioning of the bone nail device 1, and unobstructed functioning once in position within a bone.

Figures 2A, 2B, 2C:
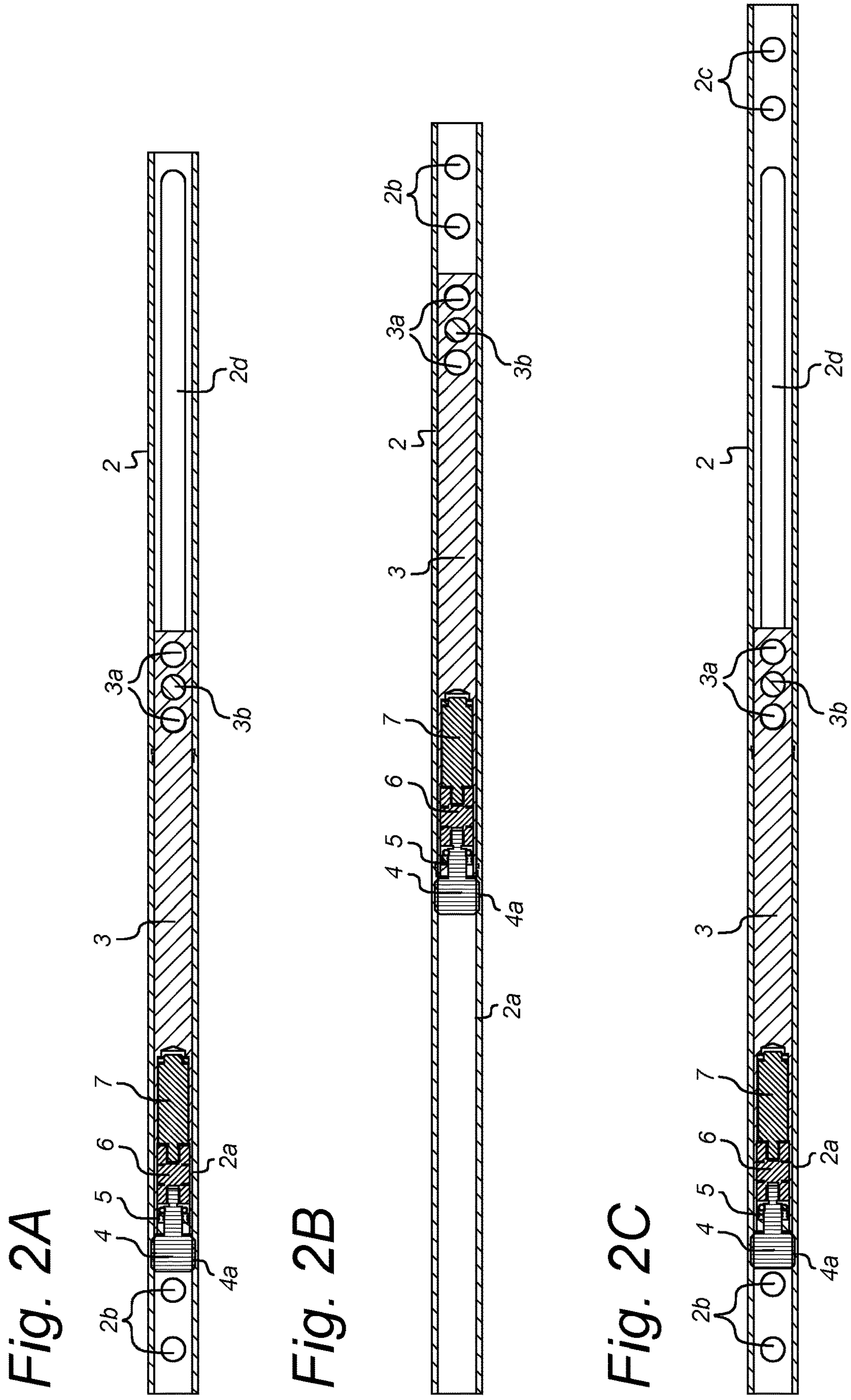
Figures 2D, 2E, 2F:
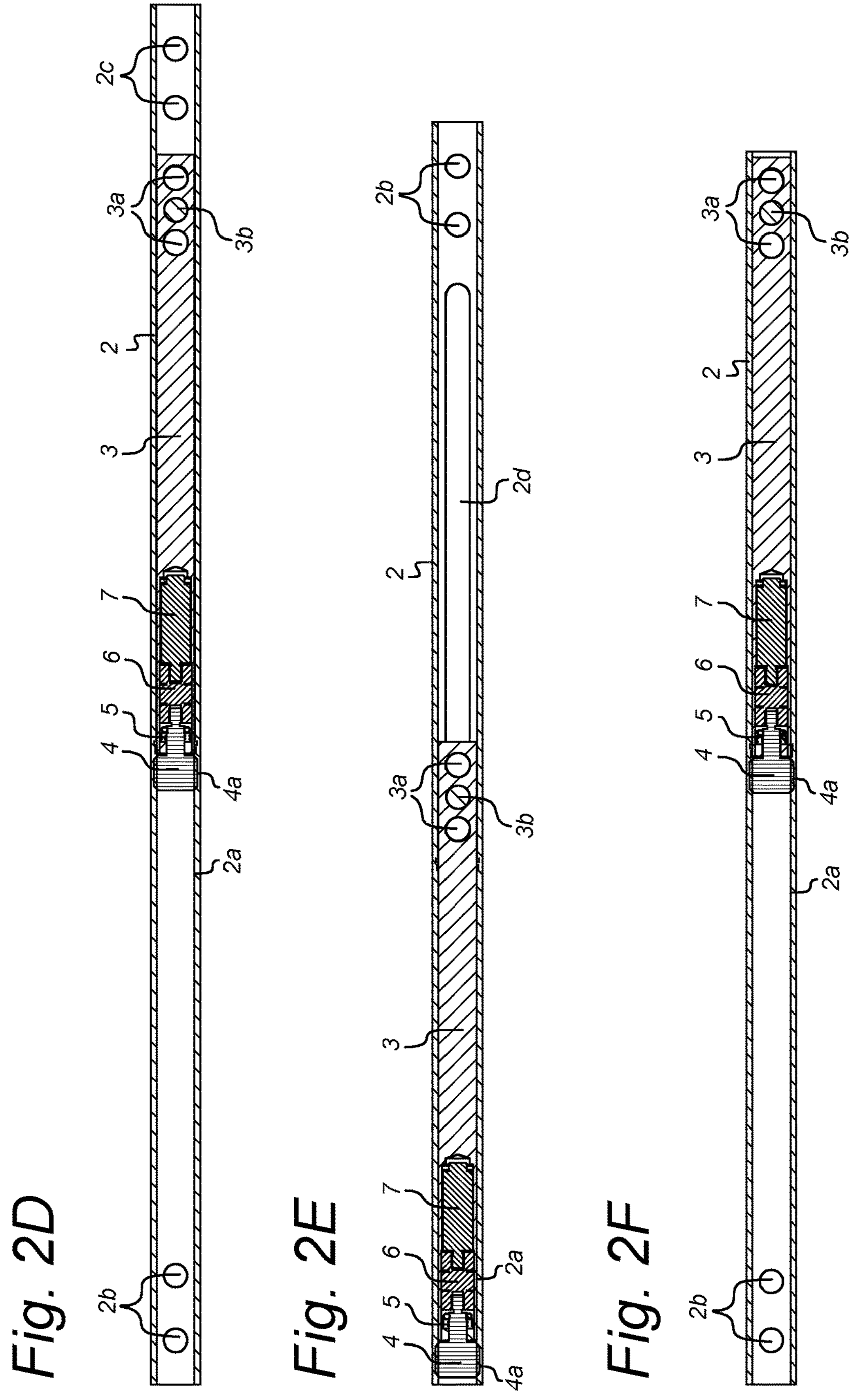

FIGS. 2A-2F show a cross sectional view of a bone nail device 1 for bone extension, bone compression and/or bone transport, according to six exemplary embodiments of the present invention. The embodiments of FIGS. 2A and 2B are specifically suitable for bone extension, the embodiments of FIGS. 2C and 2D are specifically suitable for bone transport, and the embodiments of FIGS. 2E and 2F are specifically suitable for bone compression.

In the exemplary embodiments as shown in FIGS. 2A-2F, the outer tubing 2 comprises a guiding slot 2*d*, and the inner tubing 3 comprises a guiding pin 3*b* extending through the guide slot 2*d*. The guiding pin 3*b* may comprise a cylindrical body, and the guiding slot 2*d* may comprise of a long, narrow aperture, with a width that is slightly more than the diameter of the guiding pin 3*b*, allowing a snug fit of the guiding pin 3*b* in the guiding slot 2*d*.

The combination of the guiding slot 2*d* and the guiding pin 3*b* extending through the guide slot 2*d*, correctly aligns the sliding axial movement of the inner tubing 3 relative to the outer tubing 2, and as such, allows a correct trajectory of the bone nail device 1 with no misalignment, where the trajectory of the bone extension, bone compression and/or bone transport is determined by the trajectory of the guiding slot 2*d*. In addition, as the length of the bone nail device 1 does not change if the drive unit 4, 6, 7 applies a mutual movement of the inner tubing 3 and outer tubing 2, there is no interference with surrounding bone parts or other nearby tissue during use of the bone nail device 1.

In the embodiments shown in FIGS. 2A-2F, the guiding slots 2*d* comprise a linear aperture, leading to bone extension, bone compression and/or bone transport of a linear trajectory. Furthermore, in these embodiments, the outer tubing 2 has a predetermined length, allowing positioning of the entire bone nail device 1 in a longitudinal bore drilled into an elongate bone. The bone extension operation can be effected after securing the various bone parts to the first and second bone connection members 2*b*, 3*a* by the FIG. 2A-B and FIG. 2E-F embodiments, with the benefit that there are no moving parts outside of the outer tubing 2. This lowers the risk of trauma to e.g. surrounding tissue.

In the exemplary embodiments shown in FIG. 2C-D, the outer tubing 2 comprises a third bone connection member 2*c*, positioned at an end of the outer tubing 2 axially opposite from the first bone connection member 2*b* Similar to the embodiments of the first and second bone connection members 2*b*, 3*a*, the third bone connection member 2*c* is arranged to be securely connected to at least a part of the bone or to a bone part. In a further embodiment, the third bone connection member 2*c* comprises an aperture for accommodating a transverse bone fixation screw, allowing the outer tubing 2 to securely fix to a bone part. The transport operation can be effected after securing the various bone parts to the first and second bone connection members 2*b*, 3*a*, 2*c* by the FIG. 2C-D embodiments.

Specifically, the exemplary embodiments shown in FIG. 2C-D are specifically suitable for bone transport, wherein the first and third bone connection members 2*b*, 2*c* are securely connected to the parts of the bone that remain in the same position, and the second bone connection member 3*a* is securely connected to the part of the bone that is transported.

For example, the bone nail device 1 shown in FIG. 2C is surgically implanted within the medullary cavity of a bone. The first, second and third connection members 2*b*, 3*a*, 2*c* are securely screwed onto the first, second and third parts of the bone, respectively, located at the top, middle and bottom parts of the bone, respectively. A small part of the bone is removed, e.g. due to infection, in the second part of the bone, just below the position where the second connection member 3*a* is securely connected, leaving a gap in the bone between the positions of the first and second connection members 2*b*, 3*a*. The bone is purposely fractured in the third part of the bone, just near the position where the third connection member 2*c* is securely connected. The second (now middle) part of the bone is transported, in the trajectory determined by the guiding slot 2*d*, towards the third part of the bone to fill the gap with missing bone, performing bone transport, and in tandem, the second part of the bone is transported away from the first part of the bone, creating a new gap between the first and second part of the bone for new bone to form.

In the exemplary embodiments shown in FIGS. 2B and 2E, the drive unit, i.e. the combination of drive motor 7, transport screw 4 and planetary gear 6 is positioned remote from both the first bone connection member 2*b* and the second bone connection member 3*a*. In this regard, this configuration also allows for further bone transport and/or bone compression-distraction procedures, where in the latter, e.g. two parts of a two-part fractured bone move towards one another to fill a gap in the bone and are subsequently compressed. In the embodiment shown in FIG. 2E, bone compression-distraction can be performed by securely screwing the first and second connection members 2*b*, 3*a* to the first and second part, respectively, of a two-part fractured bone, and allowing the inner tubing 3 to move within the outer tubing 2 towards the position of the first bone connection member 2*b*, thereby moving the two parts of the two-part fractured bone towards one another, performing bone compression-distraction.

Figure 3A:
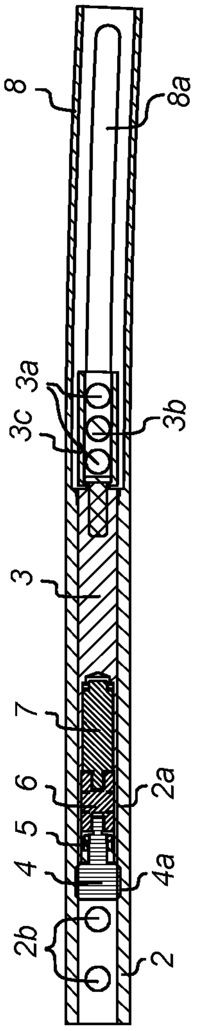
Figure 3B:
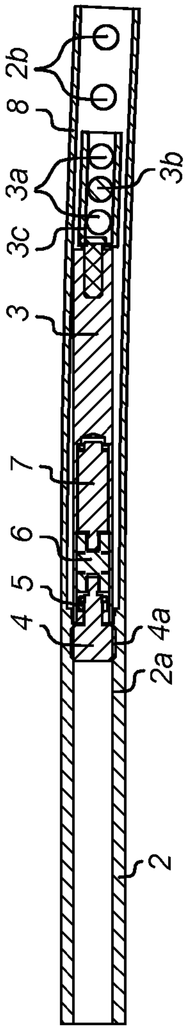
Figure 3C:
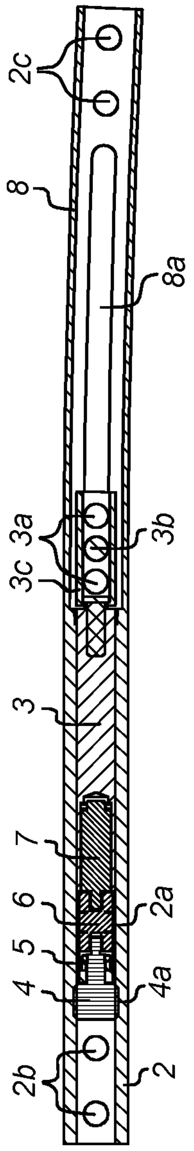
Figure 3D:
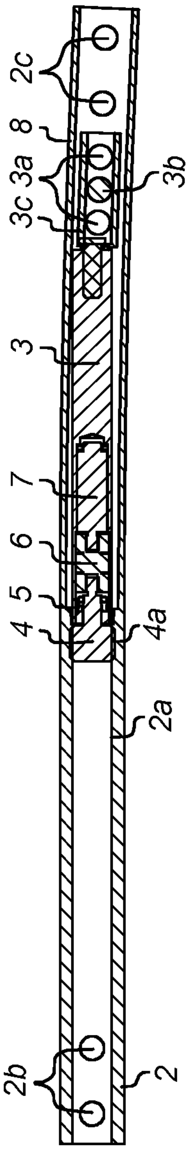
Figure 3E:
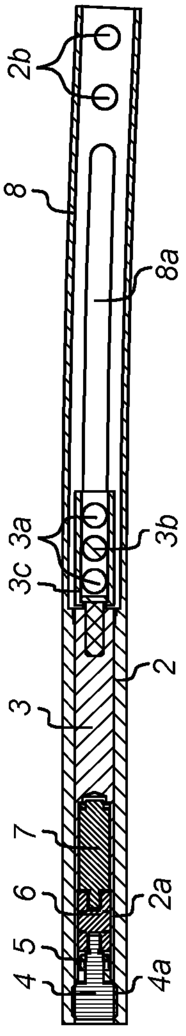
Figure 3F:
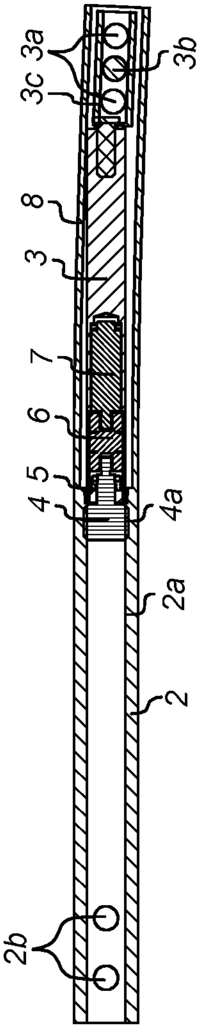

FIGS. 3A-3F show a cross sectional view of a bone nail device 1 for bone extension, bone compression and/or bone transport, according to six further exemplary embodiments of the present invention. The embodiments of FIGS. 3A and 3B are specifically suitable for bone extension, the embodiments of FIGS. 3C and 3D are specifically suitable for bone transport, and the embodiments of FIGS. 3E and 3F are specifically suitable for bone compression.

In the exemplary embodiments shown in FIGS. 3A-3F, the outer tubing 2 comprises a curved section 8 with a curved guide slot 8*a*. The curved section 8 allows bone extension, bone compression and/or bone transport with a non-linear trajectory as determined by the curved guide slot 8*a*, in comparison to the linear trajectory as determined by the linear guide slot 2*d* as described in the embodiments above with reference to FIGS. 2A-2F. This allows bone distraction procedures to be performed on bones comprising a curved (e.g. bent, arched) trajectory, e.g. a collarbone or parts of the skull.

In an embodiment, the curved guide slot 8*a* has a curvature with a radius larger than 500 mm, e.g. larger than 1000 mm. Note that a femur bone has a natural curved shape (e.g. with a curvature of 1700 mm), and this embodiment allows the movement when the bone nail device 1 is positioned in a secure manner, without risk of fracture of the (femur) bone. In an exemplary embodiment, the curved guide slot 8*a* has a curvature allowing movement of the inner tube 3 over the entire length of the curved section 8. If a difference delta between an inner diameter of the outer tubing 2 and an outer diameter of the inner tubing 3, divided by a length l of the curved section 8 is sufficiently large to accommodate for the curvature of curved guide slot 8*a* over that same length l, the inner tube 3 is able to extend over the full range of the length of the curved section 8. As shown in the embodiments of FIGS. 3B, 3D and 3F, the outer diameter of the inner tubing 3 is smaller than the inner diameter of the outer tubing 2, allowing the inner tubing 3 to extend all the way into the curved section 8 before hitting an inner wall of the outer tubing 2.

In a further embodiment, the inner tubing 3 is flexible in a longitudinal direction thereof, allowing a better and less obstructed travel of the inner tubing 3 inside the curved section 8 of the outer tubing 2. E.g. the inner tubing 3 can be made of a flexible material to accomplish this effect, e.g. carbon, plastic, or fiber-reinforced material. If the diameter of the inner tubing 3 is sufficiently small, the flexibility may even be obtained when using (surgical) metals, such as stainless steel or titanium.

In the exemplary embodiments shown in FIGS. 3A-3F, the inner tubing 3 further comprises a pivotable guiding pin connection member 3*c*, the pivotable guiding pin connection member 3*c* comprising the second bone connection member 3*a* and a guiding pin 3*b*, the guiding pin 3*b* extending through the curved guide slot 8*a*. The pivotable guiding pin connection member 3*c* allows a sliding axial movement of the inner tubing 3 relative to the outer tubing 2 in a smooth curved manner; in other wording, the pivotable guiding pin connection member 3*c* can essentially pivot and adjust the trajectory of the inner tubing 3 movement relative to the outer tubing 2 to follow the trajectory of the curved guide slot 8*a*, thereby avoiding the inner tubing 3 movement becoming jammed due to incorrect trajectory.

Otherwise, with the exception of the curved features just discussed, the embodiments discussed above for FIGS. 2A-F, including features such as the third bone connection member 2*c*, are identical to the features shown in FIGS. 3A-F, respectively, where the techniques of bone extension, bone compression and/or bone transport are also similar.

The present invention has been described above with reference to a number of exemplary embodiments as shown in the drawings. Modifications and alternative implementations of some parts or elements are possible, and are included in the scope of protection as defined in the appended claims.

The invention claimed is:

1. A bone nail device, comprising:

an outer tubing having an inner screw thread extending over at least a part of an inner surface of the outer tubing, and a first bone connection member, an inner tubing having a second bone connection member, the inner tubing being arranged inside at least a part of the outer tubing to allow a sliding axial relative movement, wherein the bone nail device is configured for intramedullary placement within a medullary cavity of a bone, and a drive unit, the drive unit comprising a drive motor arranged in the inner tubing and fixedly attached to the inner tubing, a transport screw having an outer screw thread engaging the inner screw thread of the outer tubing for sliding axial movement of the inner tubing relative to the outer tubing by rotation of the transport screw, and a planetary gear having an input end connected to the drive motor and an output end connected to the transport screw.

2. The bone nail device according to claim 1, wherein the first and/or second bone connection member comprise an aperture for accommodating a transverse bone fixation screw.

3. The bone nail device according to claim 1, further comprising a bearing attached to the transport screw for withstanding axial load.

4. The bone nail device according to claim 1, wherein the combination of drive motor, transport screw and planetary gear is positioned between the first bone connection member and the second bone connection member.

5. The bone nail device according to claim 1, wherein the outer tubing comprises a guiding slot, and the inner tubing comprises a guiding pin extending through the guide slot.

6. The bone nail device according to claim 5, wherein the combination of drive motor, transport screw and planetary gear is positioned remote from both the first bone connection member and the second bone connection member.

7. The bone nail device according to claim 1, wherein the outer tubing comprises a third bone connection member, positioned at an end of the outer tubing axially opposite from the first bone connection member.

8. The bone nail device according to claim 7, wherein the third bone connection member comprises an aperture for accommodating a transverse bone fixation screw.

9. The bone nail device according to claim 1, wherein the outer tubing comprises a curved section with a curved guide slot.

10. The bone nail device according to claim 9, wherein the inner tubing is flexible in a longitudinal direction thereof.

11. The bone nail device according to claim 9, the inner tubing further comprising a pivotable guiding pin connection member, the pivotable guiding pin connection member comprising the second bone connection member and a guiding pin, the guiding pin extending through the curved guide slot.

12. The bone nail device according to claim 9, wherein the curved guide slot has a curvature with a radius larger than 500 mm.

13. The bone nail device according to claim 1, wherein the drive motor is an electric motor.

14. The bone nail device according to claim 1, wherein the drive motor is a magnetic motor driven by an external magnetic drive actuator.

15. The bone nail device according to claim 1, wherein the planetary gear is a reduction gear.

* * * * *